(12) United States Patent
Sharma

(10) Patent No.: US 12,310,778 B2
(45) Date of Patent: May 27, 2025

(54) APPARATUS AND METHODS FOR IMPROVED DENOISING IN MAGNETIC RESONANCE IMAGING BASED ON METAL ARTIFACT REDUCTION

(71) Applicant: CANON MEDICAL SYSTEMS CORPORATION, Tochigi (JP)

(72) Inventor: Samir Dev Sharma, Vernon Hills, IL (US)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 428 days.

(21) Appl. No.: 17/690,834

(22) Filed: Mar. 9, 2022

(65) Prior Publication Data

US 2023/0284995 A1    Sep. 14, 2023

(51) Int. Cl.
*A61B 6/00* (2024.01)
*G06T 7/00* (2017.01)

(52) U.S. Cl.
CPC .......... *A61B 6/5241* (2013.01); *A61B 6/5258* (2013.01); *G06T 7/0012* (2013.01); *G06T 2207/10088* (2013.01)

(58) Field of Classification Search
CPC ... A61B 6/5241; A61B 6/5258; G06T 7/0012; G06T 2207/10088; G06T 2207/20212; G06T 5/50; G06T 5/70; G01R 33/56536; G01R 33/56563; G01R 33/4835
USPC .................................................. 382/100, 131
See application file for complete search history.

(56) References Cited

U.S. PATENT DOCUMENTS

| 2015/0362576 | A1* | 12/2015 | Jurrissen | .......... G01R 33/56536 324/309 |
| 2017/0076043 | A1* | 3/2017 | Dormer | .................. G16H 40/67 |
| 2017/0269179 | A1 | 9/2017 | Horng | |

OTHER PUBLICATIONS

Wenmiao Lu; "Compressive slice encoding for metal artifact correction in MRI", Beckman institute for advanced science and technology, University of Illinois; 2013.
(Continued)

*Primary Examiner* — Sheela C Chawan
(74) *Attorney, Agent, or Firm* — Oblon, McClelland, Maier & Neustadt, L.L.P.

(57) ABSTRACT

The present disclosure relates to a method and apparatus correcting a metal artifact in magnetic resonance imaging (MRI) data. The method and apparatus acquire plural slices along a slice direction of a scanned region associated with a body part, estimate a spatial extent of a signal dispersion of the acquired plural slices along the slice direction, and combine the signal of the acquired plural slices along the slice direction based on the estimated spatial extent of the signal dispersion to generate a reconstructed image of the scanned region. The method and apparatus may identify, from the acquired plural slices along the slice direction, a slice with a highest pixel intensity; and identify at least one neighboring slice neighboring the slice with the highest pixel intensity based on a 3D spatial dipole response function, wherein combining the signal of the acquired plural slices along the slice direction based on the estimated spatial extent of the signal dispersion comprises combining (a) the signal of the slice with the highest pixel intensity and (b) the signal of the at least one neighboring slice.

13 Claims, 14 Drawing Sheets

(56) References Cited

OTHER PUBLICATIONS

Harder, den, J. M.; "Metal implant artifact reduction in magnetic resonance Imaging", Eindhoven University of Technology; Jan. 1, 2015.

Theresa Bachschmidt aus Roth; "Magnetic resonance imaging in proximity to metal implants at 3 tesla"; Julius-Maximilians-Universität Würzburg; 2015.

Iman Khodarahmi et. al.; "Metal about the hip and artifact reduction techniques: from basic concepts to advanced imaging"; Jun. 2019.

* cited by examiner

APPARATUS AND METHODS FOR IMPROVED DENOISING IN MAGNETIC RESONANCE IMAGING BASED ON METAL ARTIFACT REDUCTION

BACKGROUND

Field of the Disclosure

The present disclosure relates to a method, apparatus, and non-transitory computer-readable storage medium for improved denoising in magnetic resonance imaging based on metal artifact reduction.

Description of the Related Art

Various medical imaging systems generate images of internal organs and tissues of a patient's body. For example, magnetic resonance imaging (MRI) uses radio waves, magnetic fields, and magnetic-field gradients to generate images of internal organs and tissues. Once these images have been generated, a physician can use the images for diagnosing patient injuries or diseases.

A metal implant or a metal object present in a patient's body during an MRI scan presents several challenges. One major challenge is to correct or at least reduce metal artifacts from the data acquired by the MRI scan. Metal artifact reduction methods utilized to correct the metal artifacts from the data acquired by the MRI scan require acquiring data along different axes in order to resolve the signal distortion that occurs due to the strong susceptibility of the metal implant. Such metal artifact reduction methods take into consideration a plurality of regions along the different axes to resolve the signal distortion. However, many such regions often only include noise. Accordingly, known metal artifact reduction methods do not provide an effective approach to reduce or correct the metal artifacts.

FIG. 1 illustrates that, as part of a Magnetic Resonance Imaging process, data can acquired along different axes in order to better address signal distortion that can occur due to the strong susceptibility of a metal implant. In a slice encoding for metal artifact correction (SEMAC) acquisition process, a two-dimensional (2D) slice is excited and then the 2D slice is encoded into a three-dimensional (3D) volume. The result of the SEMAC acquisition is a four-dimensional (4D) volume 100 in dimensions (x, y, z, slice). FIG. 1 illustrates Z-axis 104 and the slice axis 102. Further, x and y planes are not illustrated in FIG. 1, however it is understood to one skilled in the art in 4D volume axial system x and y axis would be passing into the FIG. 1. Additionally, coil dimension has been omitted for simplicity.

Further, a SEMAC reconstruction operation is performed by a SEMAC combination operation. As part of the SEMAC combination, for each (x,y) location, all data along a line 106 in the (z,slice) plane is combined. This SEMAC combination can be simply done by calculating a root-sum-of-squares (RSS) along a line 106 in the (z, slice) plane. The simple RSS combination introduces noise because many slices on the line 106 contain mostly noise. Accordingly, a primary technical problem is to develop a method for combining image data that preserves the signal while minimizing the noise.

The foregoing "Background" description is for the purpose of generally presenting the context of the disclosure. Work of the inventors, to the extent it is described in this background section, as well as aspects of the description which may not otherwise qualify as prior art at the time of filing, are neither expressly nor impliedly admitted as prior art against the present invention.

SUMMARY

The present disclosure relates to an apparatus, method, and non-transitory computer-readable storage medium for image quality improvement based on noise reduction due to metal artifacts.

According to an embodiment, the present disclosure relates to a method for correcting an artifact (e.g., a metal artifact) in magnetic resonance imaging (MRI) data, the method including, but not limited to: acquiring plural slices along a slice direction of a scanned region associated with a body part; estimating a spatial extent of a signal dispersion of the acquired plural slices along the slice direction; and combining the signal of the acquired plural slices along the slice direction based on the estimated spatial extent of the signal dispersion to generate a reconstructed image of the scanned region.

According to an embodiment, the present disclosure relates to an apparatus for correcting an artifact (e.g., a metal artifact) in magnetic resonance imaging (MRI) data, the apparatus including, but not limited to, processing circuitry configured to acquire plural slices along a slice direction of a scanned region associated with a body part; estimate a spatial extent of a signal dispersion of the acquired plural slices along the slice direction; and combine the signal of the acquired plural slices along the slice direction based on the estimated spatial extent of the signal dispersion to generate a reconstructed image of the scanned region.

According to an embodiment, the present disclosure relates to a non-transitory computer-readable storage medium storing computer-readable instructions that, when executed by a computer, cause the computer to perform a method for correcting an artifact (e.g., a metal artifact) in magnetic resonance imaging (MRI) data, the method including, but not limited to: acquiring plural slices along a slice direction of a scanned region associated with a body part; estimating a spatial extent of a signal dispersion of the acquired plural slices along the slice direction; and combining the signal of the acquired plural slices along the slice direction based on the estimated spatial extent of the signal dispersion to generate a reconstructed image of the scanned region.

The foregoing paragraphs have been provided by way of general introduction and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A complete appreciation of the disclosure and many of the attendant advantages thereof will be readily obtained as the same becomes better understood by reference to the following detailed description when considered in connection with the accompanying drawings, wherein.

DETAILED DESCRIPTION

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

Figure 1:
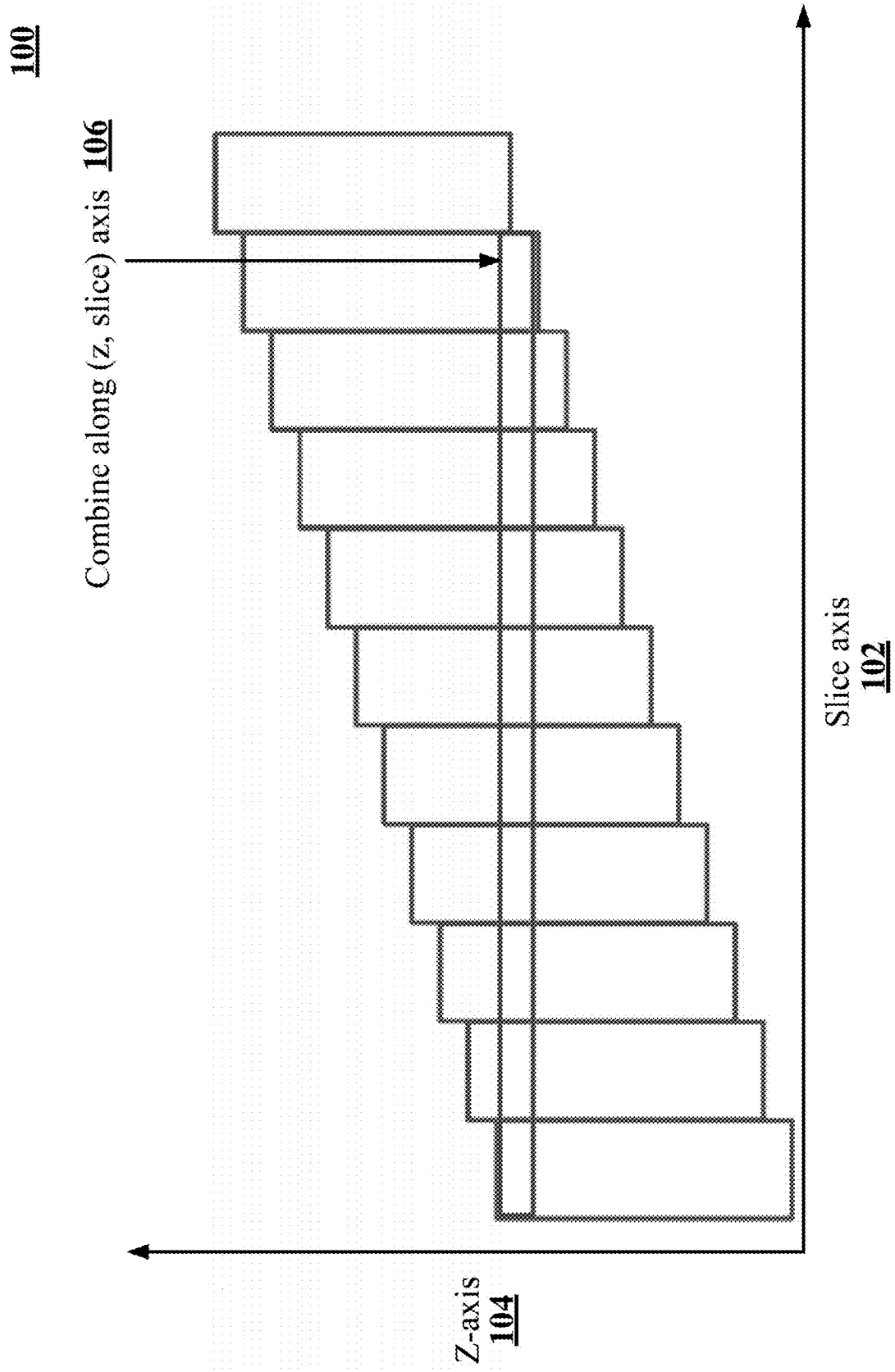
FIG. 1 is an illustration of acquiring and combining data along plural slices for metal artifact correction as part of a known slice encoding for metal artifact correction (SEMAC) process.
Figure 2:
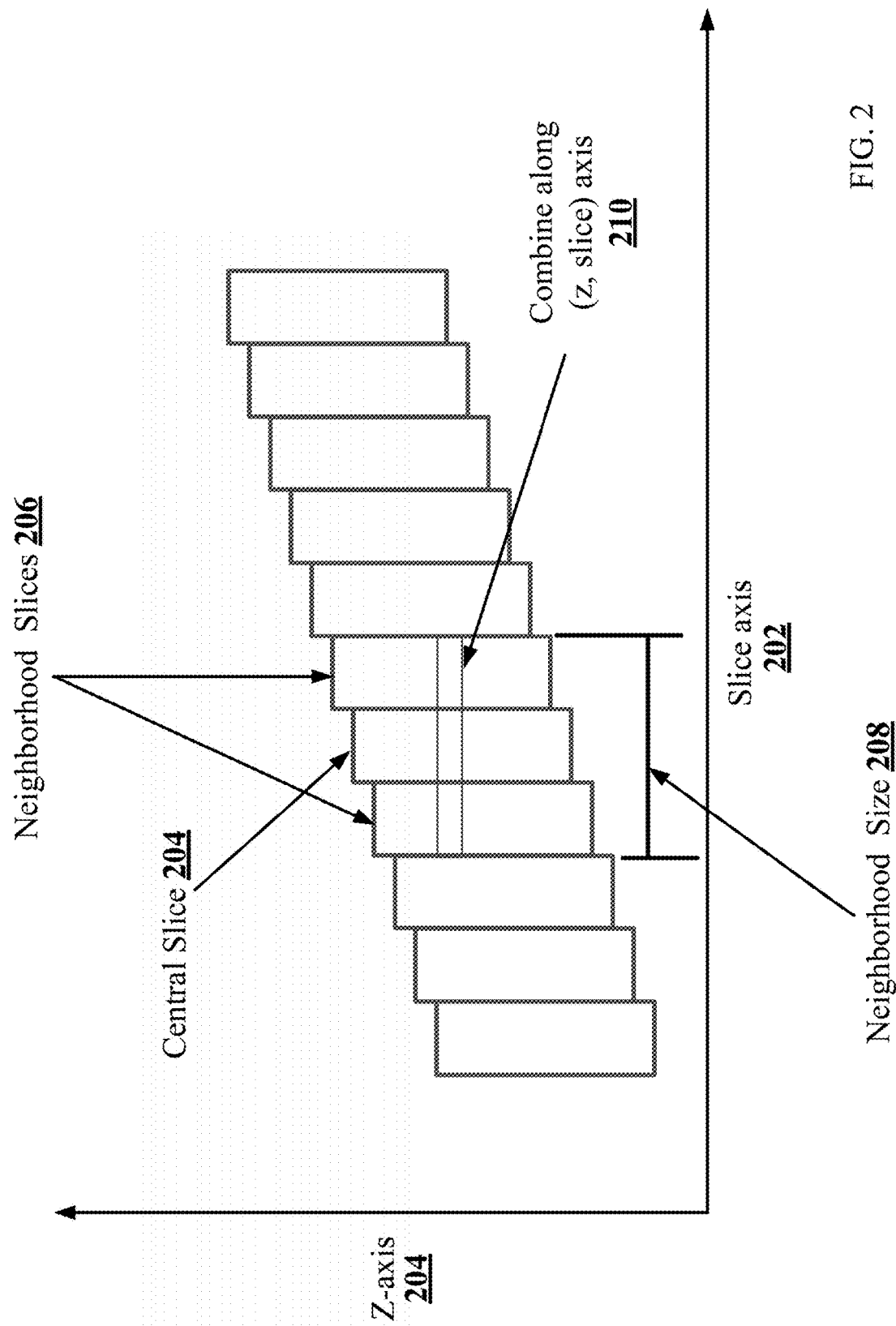
FIG. 2 is an illustration of combining acquiring data along a predefined neighborhood of slices surrounding a central slice for metal artifact correction, according to an exemplary embodiment of the present disclosure.

Now referring to FIG. 2, a method for improved denoising in magnetic resonance imaging (MRI) based on metal artifact reduction is illustrated. Similar to FIG. 1, during data acquisition, a two-dimensional (2D) slice is excited, and then the 2D slice is encoded into a three-dimensional (3D) volume. The result of the data acquisition is a four dimensional (4D) volume 100 in dimensions (x, y, z, slice). FIG. 2 illustrates Z-axis 204 and the slice axis 202. In FIG. 2, the acquired slices are analyzed to focus the correction on a localized number of slices as opposed to all the slices that share a particular part of an area (in the z-axis dimension).

As part of the combination process, a central slice 212 is first determined. The central slice 212 may be a slice with the highest signal intensity (i.e., the central slice 212 indicates a likely location of a metal implant in a patient's body). Next, a neighborhood size 208 is determined by utilizing a full width at half maximum (FWHM) of dipole response function (explain below with reference to FIG. 4). Upon determining the neighborhood size 208, the slices included in the neighborhood size 208 are identified. This example, the neighborhood slices are identified as 206. Accordingly, for each (x,y) location, all data along a line 210 in the (z, slice) plane is combined. This combination can be simply done by calculating a root-sum-of-squares (RSS) along a line 210 in the (z,slice) plane. As illustrated, only a central slice 212 that has a highest intensity signal and its neighbouring slices 206 are taken into consideration as part of the combination. By only considering the slices 212 and 206, other slices along the slice axis 202 that do not provide a location of the metal implant in the patient's body are not utilized thus providing better estimation results for metal artifact reduction.

This neighborhood combination technology builds on the fact that the signal dispersion in voxels that are subject to metal-induced susceptibility is limited. An advantage of this technology is that the signal dispersion is closely clustered (explained with reference to FIGS. 3 and 4 below) (as opposed to being randomly distributed). This is an effect of the localized nature of the dipole response function. The dipole response function provides a mathematical description for how a high susceptibility source (e.g., metal) will affect the B0 field. A high susceptibility object will cause signal dispersion, however the dispersion will still be localized along the line in the (z,slice) plane. Further, the extent to be considered can be determined using information about the dipole response function. For example, a full width at half maximum (FWHM) is calculated and using the slice thickness of the acquisition, those points that are within the FWHM can be retained for the combination.

Figure 3:
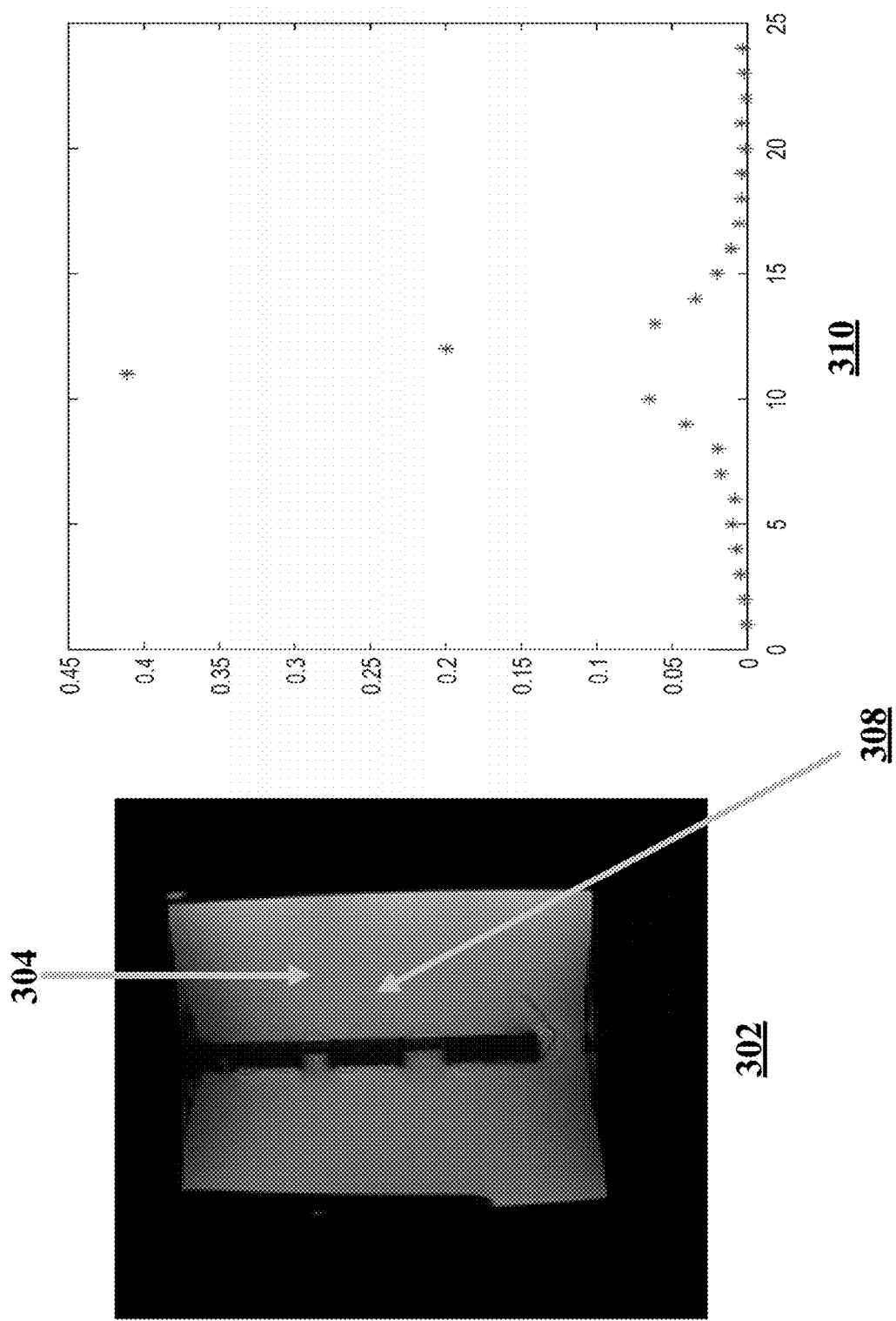
FIG. 3 is an illustration of positioning of voxel values for a reference region with a known medium, according to an exemplary embodiment of the present disclosure.

Specifically, FIG. 3 illustrates a MRI scanned reference image 302 generated under a controlled environment to explain the signal dispersion for reference region in a known medium based on voxel values for a reference region with water/tissue. The known medium may be water or tissue of an organ of a patient. By way of example, the reference region may be a point 308 in a water medium and the signal dispersion of the point 308 is represented by the graphical representation 310. The graphical representation 310 represents the signal dispersion of the point 308 across x-axis and y-axis. Here the x-axis represents slice axis parameter and the y-axis represents the signal intensity parameter. Accordingly, graphical representation 310 illustrates that for the known medium of water the signal dispersion is mostly clustered and localized.

Figure 4:
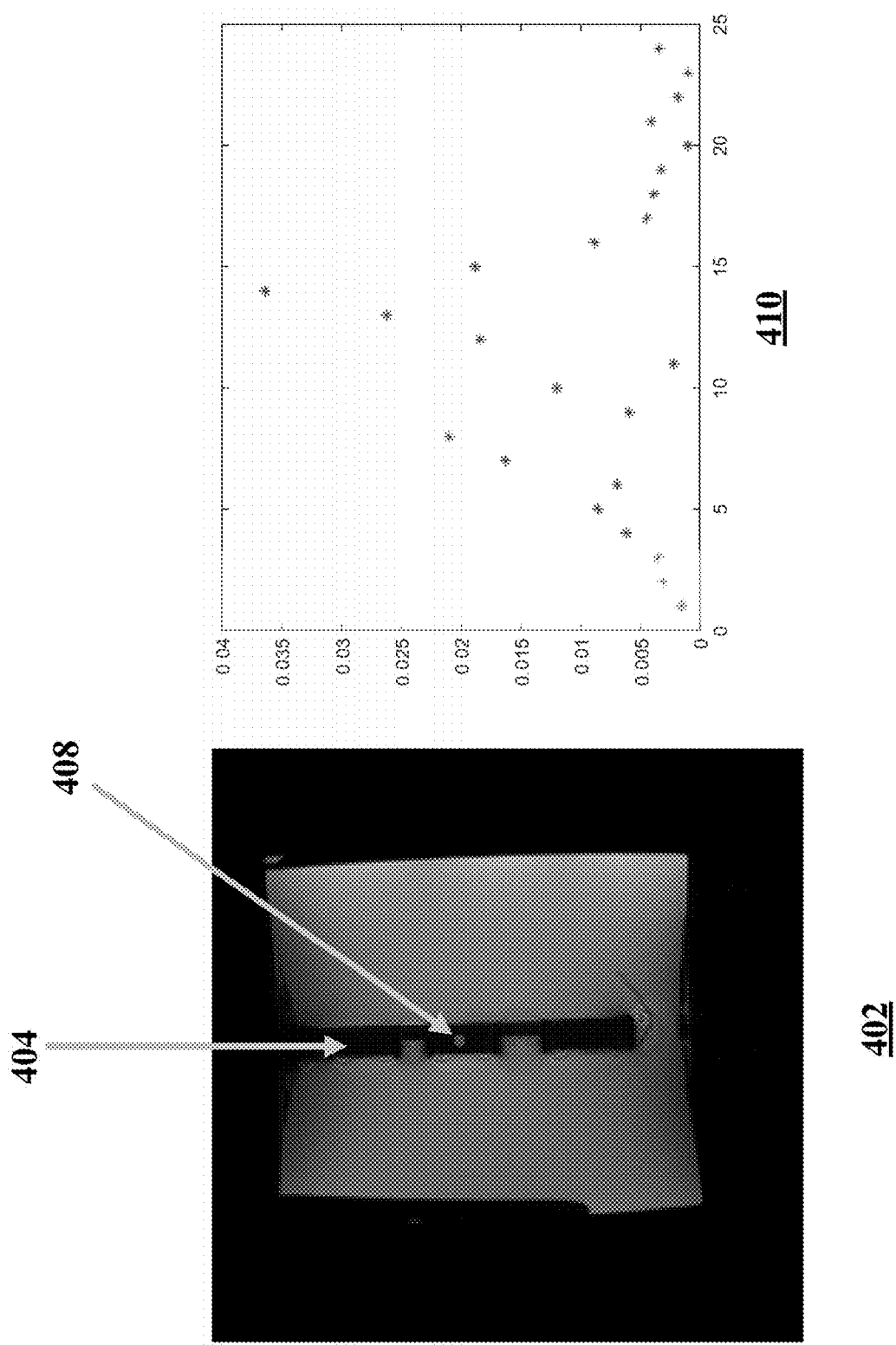
FIG. 4 is an illustration of positioning of voxel values for another reference region with noise, according to an exemplary embodiment of the present disclosure.

Further, FIG. 4 illustrates a MRI scanned reference image 402 generated under a controlled environment to explain the signal dispersion for reference region in a known medium based on voxel values for another reference region with metal medium. The known medium may be a metal implant in a patient body. By way of example, the reference region may be a point 408 in a metal implant and the signal dispersion of the point 408 is represented by the graphical representation 410. Accordingly, 410 illustrates that a dipole response function provides a mathematical description for a high susceptibility medium region (e.g., metal implant region) will affect the B0 field. Thus the metal implant region (also referred to as a high susceptibility object) will cause signal dispersion, however the dispersion will still be localized along the line in the (z,slice) plane. This signal dispersion of 410 is not randomly distributed. The clustering of the signal dispersion is consistent with the MR physics using a known dipole response function. Further, the extent to be considered can be determined using information about the dipole response function. For example, a full width at half maximum (FWHM) is calculated and using the slice thickness of the acquisition, those points that are within the FWHM can be retained for the combination purposes (explained in detail below with reference to FIG. 5). Referring back to FIG. 2, utilizing the FWHM and the slice thickness of the acquisition the neighborhood size 208 is calculated.

Figure 5:
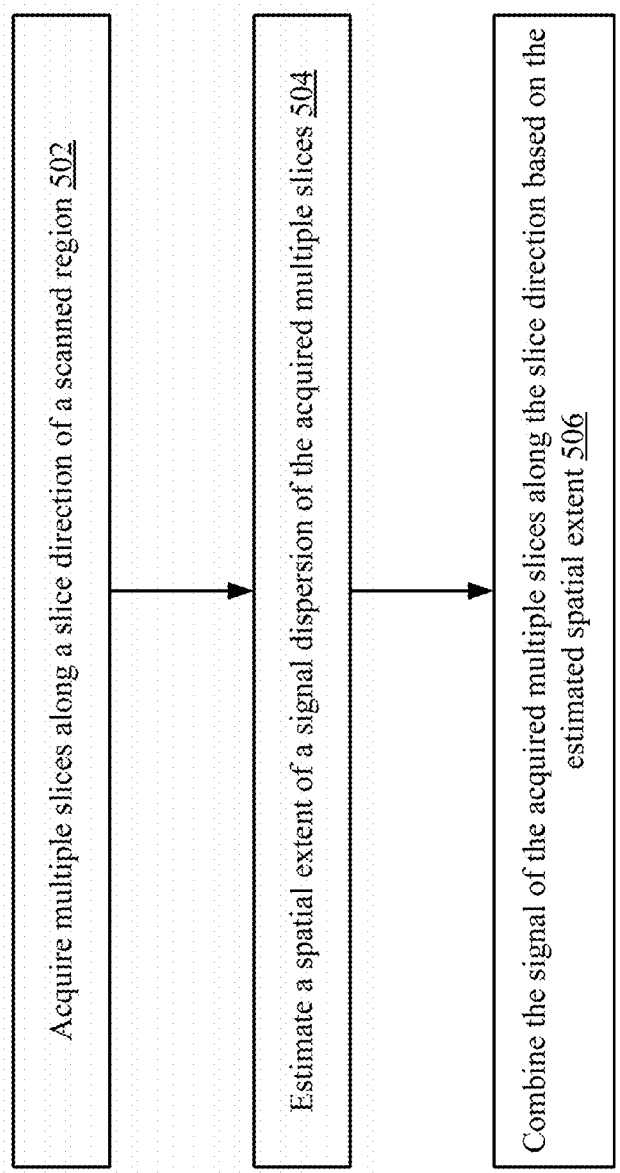
FIG. 5 is a flow diagram of a method for improved denoising in magnetic resonance imaging (MRI) based on metal artifact reduction, according to an exemplary embodiment of the present disclosure.

Turning now to the FIG. 5, FIG. 5 is a flow diagram of a method for improved denoising in magnetic resonance imaging (MRI) based on metal artifact reduction. The flow diagram of FIG. 5 describes method 500.

At step 502, plural slices along a slice axis 208 of a scanned region are acquired as illustrated and explained above with reference to FIG. 2.

At step 504, as part of the combination, a spatial extent of the signal dispersion of the acquired plural slices is estimated. As part of the combination, a central slice 212 is first determined. The central slice 212 may be a slice with the highest signal intensity i.e. the central slice 212 indicates a location of a metal implant in a patient's body. Next, a neighborhood size 208 (also referred to as a spatial extent of the signal dispersion) is estimated (e.g., by utilizing a full width at half maximum (FWHM) of dipole response function). The number of slices in the neighborhood can be as small as one neighboring slice and as large as one less than the full number of slices. In a preferred embodiment for a clinical scan using a 3 mm slice thickness, a neighborhood size of two slices in either direction of the center slice is utilized.

At step 506, the signal of the acquired plural slices along the slice direction based on the estimated spatial extent are combined. Specifically, upon determining the neighborhood size 208, the slices included in the neighborhood size 208 are identified. This example, the neighborhood slices are identified as 206. Accordingly, for each (x,y) location, all data along a line 210 in the (z,slice) plane is combined. This combination can be simply done by calculating a root-sum-of-squares (RSS) along a line 210 in the (z,slice) plane. Thus, in this technology only a central slice 212 that has a highest intensity signal and its neighbouring slices 206 are taken into consideration as part of the combination. By only considering the slices 212 and 206, other slices along the slice axis 202 that do not provide a location of the metal implant in the patient's body are not utilized thus providing better estimation results for metal artifact reduction.

Figure 6A:
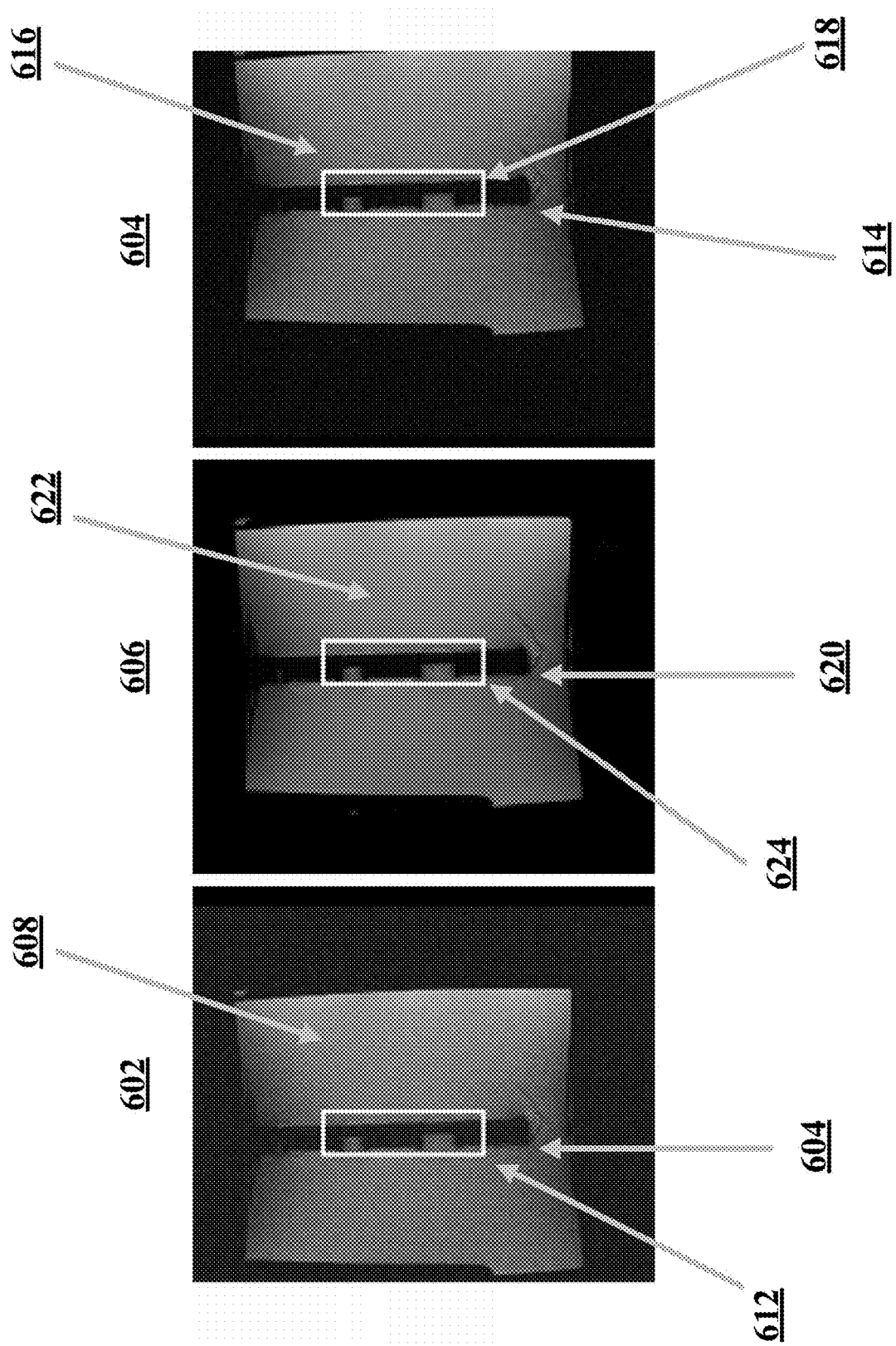
FIG. 6A is an illustration of a scanned image (right) after applying the method of FIG. 1 for noise reduction and after applying a known metal artifact reduction method for noise reduction (left) in comparison with a reference image (center)

Now, FIG. 6A is explained with reference to FIGS. 1 and 2. Specifically, FIG. 6A illustrates (1) an image 602 generated after applying the method of FIG. 1 for noise reduction along the line 106 to a scanned image and (2) an image 604 generated after applying the method of FIG. 2 for noise reduction along the line 210 to the scanned image. Further, an image 606 is a reference image generated in ideal conditions (with no noise) for the purpose of illustrating the differences between images 602 and 604.

The image 602 is an image generated in response to applying the metal artifact reduction method of FIG. 1. Further, a region 604 indicates a metal implant and a region 608 indicates a water/tissue region of the scanned image. The image 602 further illustrates a region of interest covered by the box 608 and explained in detail in FIG. 6B.

The image 604 is an image generated in response to applying the metal artifact reduction method of FIG. 2. Further, a region 614 indicates the metal implant and a region 616 indicates a water/tissue region of the scanned image. The image 604 further illustrates a region of interest covered by the box 618 and explained in detail in FIG. 6B.

The image 606 is a reference image as explained earlier. Further, a region 620 indicates the metal implant and a region 622 indicates a water/tissue region of the scanned image. The image 606 further illustrates a region of interest covered by the box 624 and explained in detail in FIG. 6B.

Figure 6B:
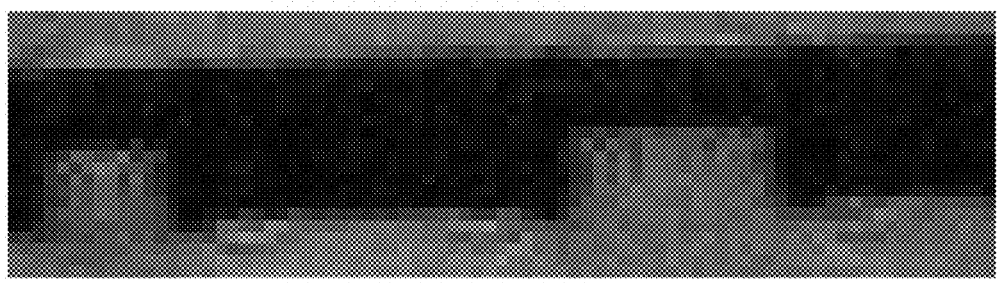
FIG. 6B is a series of enlarged images showing the highlighted areas of FIG. 6A.
Figure 6B:
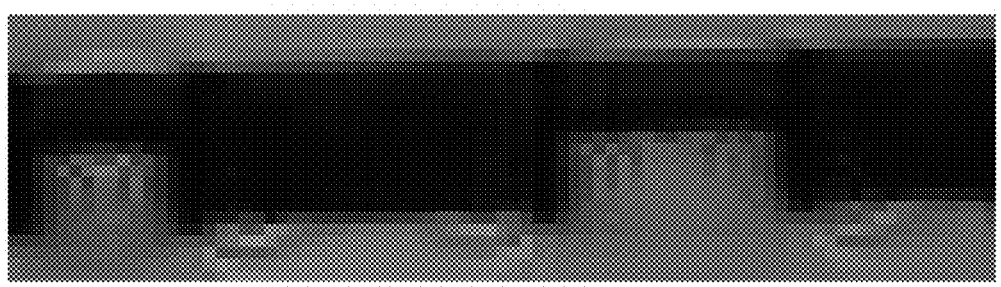
Figure 6B:
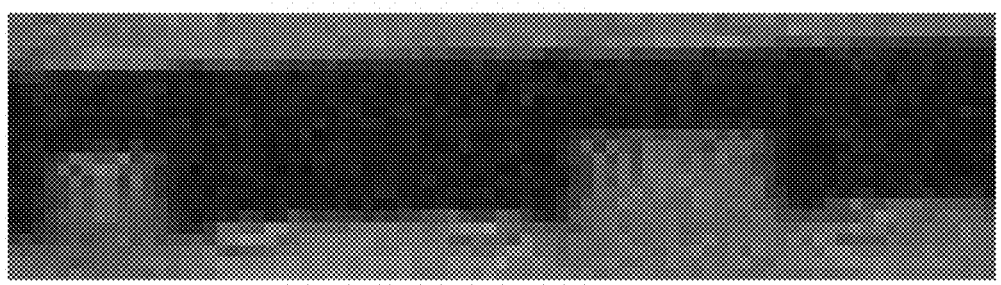

Now, FIG. 6B illustrates an enlarged image for the regions of interest 612, 618, and 624 of FIG. 6A. As seen in FIG. 6B when the region of interest 612 is compared with the region of interest 618, the region of interest of 618 has significantly less noise. Further, comparing the region of interest 618 with 624, it is illustrated that the noise difference between the region of interest of 618 and the region of interest of 624 of the reference image is reduced. Accordingly, this illustrates that the image 604, the image generated in response to applying the metal artifact reduction method of FIG. 2, provides a measurable reduction in noise and thus provides a more efficient method of metal artifact reduction.

Figure 6C:
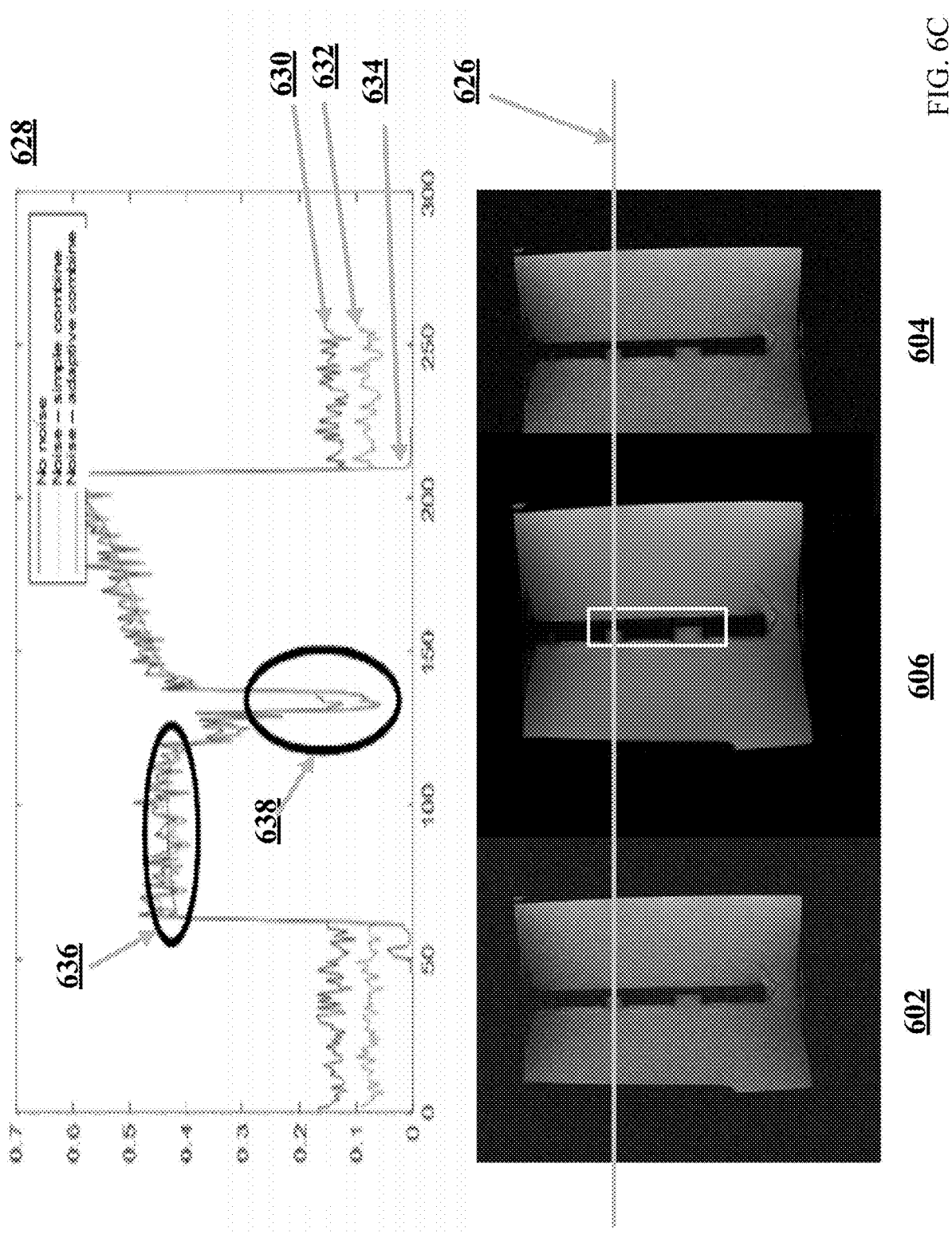
FIG. 6C illustrates a set of comparative signals corresponding to one position on the images of FIG. 6A.

FIG. 6C illustrates signal generated at a position on the images 602, 604, and 606 of FIG. 6A. FIG. 6C illustrates a line 626 passing through the images 602, 604, and 606. Further, a graphical illustration 628 indicates signals generated corresponding a location of the line 626 on the images 602, 604, and 606. By way of example, a signal 630 is generated corresponding to the location of the line 626 on the image 602, a signal 632 is generated corresponding to the location of the line 626 on the image 604, and the signal 634 is generated corresponding to the location of the line 626 on the image 606. The bubbles 636 and 638 highlight locations where the noise reduction methods yield very different results with the method of FIG. 2 providing results closer to the target no noise signal. The 636 bubble demonstrates that the method of FIG. 2 preserves the high signal as well as the known method of FIG. 1. The 638 bubble shows that in a region with low signal (i.e., in a region of noise), the method of FIG. 2 provides a result closer to the target no noise signal. Generally, the method of FIG. 2 is intended to show preserving the signal when there is high signal but reduces noise in the low signal (i.e. noise) regions.

Figure 7A:
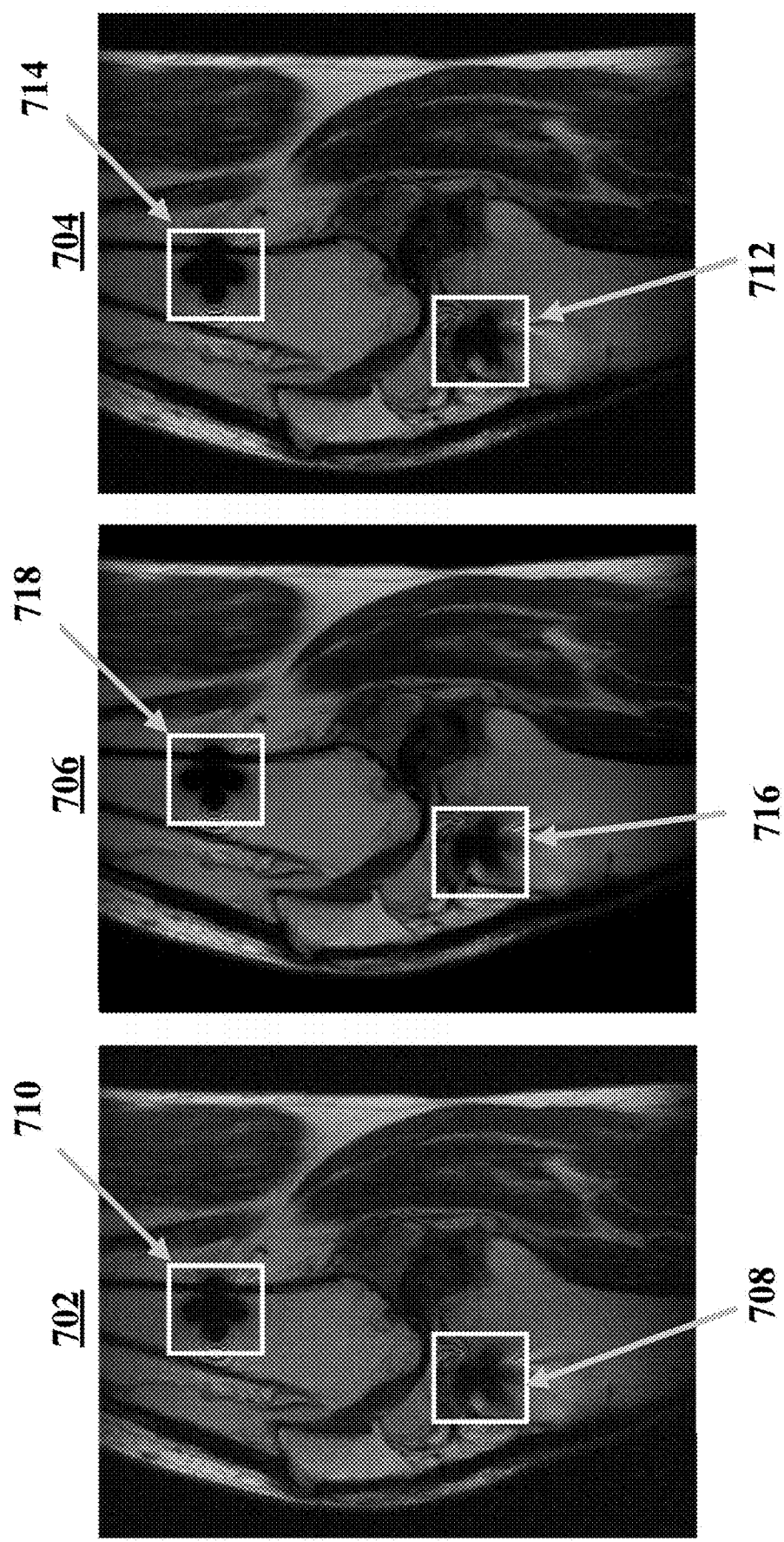
FIG. 7A is an illustration of a scanned image of a body part after applying the method of FIG. 5 for noise reduction (right) and after applying a known metal artifact reduction method for noise reduction (left) in comparison with a reference image (center)

Now, FIG. 7A is explained with reference to FIGS. 1 and 2. Specifically, FIG. 7A illustrates (1) an image 702 generated after applying the method of FIG. 1 for noise reduction along a line passing through a region of interest 708 of a scanned image and (2) an image 704 generated after applying the method of FIG. 2 for noise reduction through a corresponding region of interest 712 of the scanned image. Further, an image 706 is a reference image generated in ideal conditions (with no noise) for the purpose of illustrating the differences between images 702 and 704.

The image 702 is an image generated in response to applying the metal artifact reduction method of FIG. 1. Further, a region of interest 708 indicates a first metal implant region of interest and a region of interest 710 indicates a second metal implant region of interest in the scanned image. By way of example, the metal implant is a metal screw although any other metal implant may also be included. The regions of interest 708 and 710 are explained in detail in FIGS. 7B-7C, respectively.

The image 704 is an image generated in response to applying the metal artifact reduction method of FIG. 2. Further, a region of interest 712 indicates a first metal implant region of interest and a region of interest 714 indicates a second metal implant region of interest in the scanned image. The regions of interest 712 and 714 are explained in detail in FIGS. 7B-7C, respectively. The image 706 is a reference image as explained earlier. Further, a region of interest 716 indicates the first metal implant region of interest and a region of interest 718 indicates the second metal implant region of interest in the scanned image.

Figure 7B:
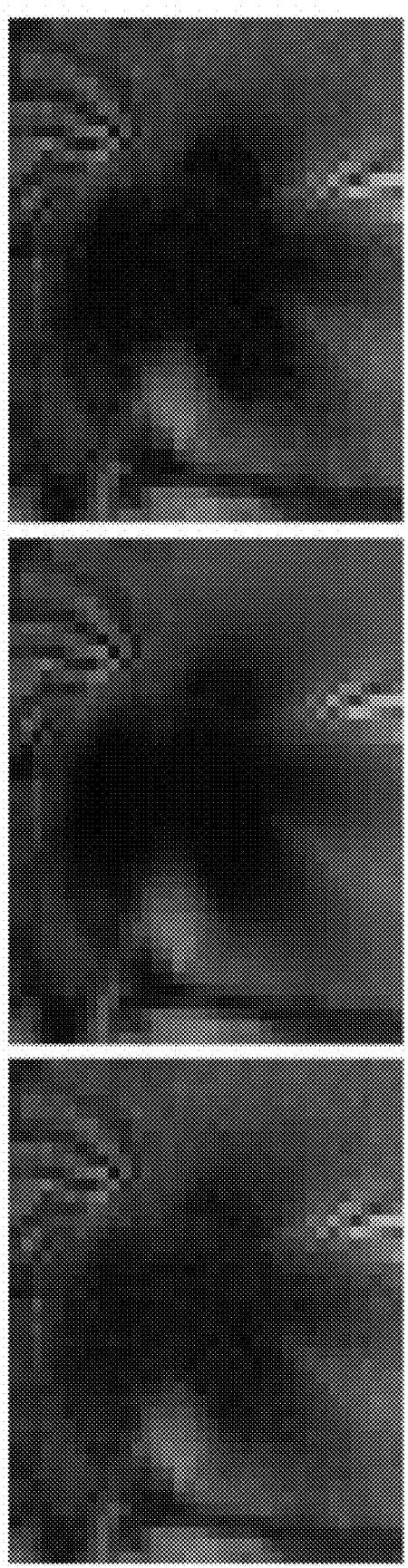
FIG. 7B is a series of enlarged images showing the lower highlighted areas of FIG. 7A.
Figure 7C:
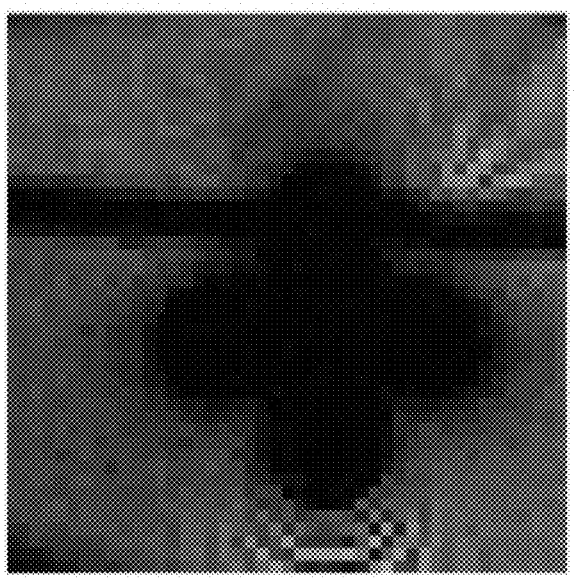
FIG. 7C is a series of enlarged images showing the upper highlighted areas of FIG. 7A.
Figure 7C:
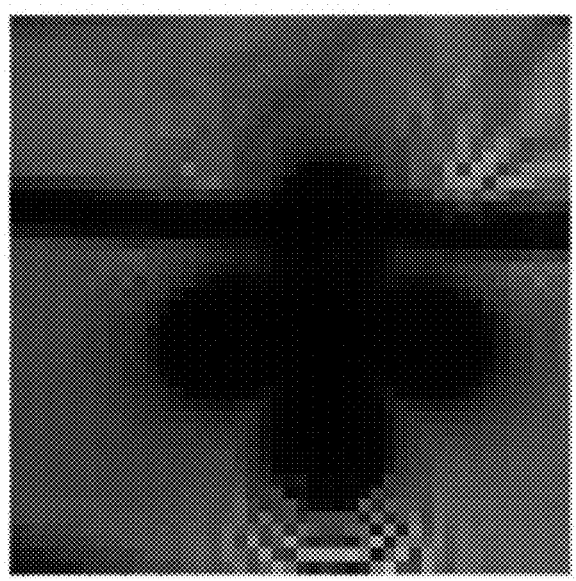
Figure 7C:
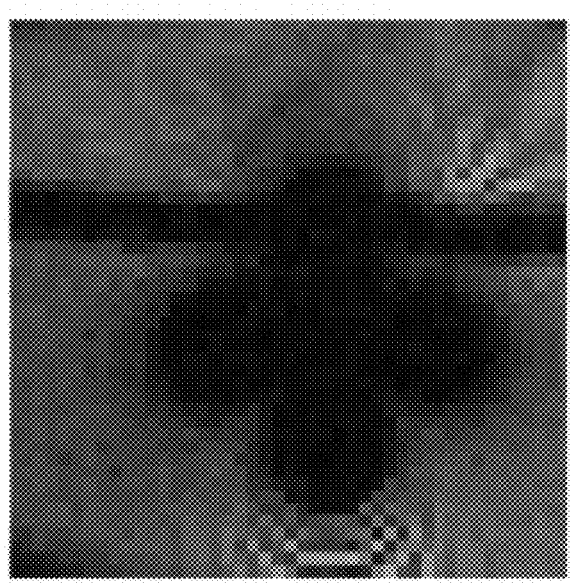

FIG. 7B illustrates an enlarged image for the regions of interest 708, 716, and 712 of FIG. 7A. As seen in FIG. 7B when the region of interest 708 is compared with the region of interest 712, the region of interest of 712 has measurably less noise. Further, comparing the region of interest 716 with 712, it is illustrated that the noise difference between the region of interest of 716 and the region of interest of 712 of the reference image is measurably less. Now, FIG. 7C illustrates an enlarged image for the regions of interest 710, 714, and 718 of FIG. 7A. As seen in FIG. 7C when the region of interest 714 is compared with the region of interest 710, the region of interest of 714 has measurably less noise. Further, comparing the region of interest 718 with 714, it is illustrated that the noise difference between the region of interest of 718 and the region of interest of 714 of the reference image is measurably less. Accordingly, FIGS. 7B and 7C illustrate that the image 704, the image generated in response to applying the metal artifact reduction method of FIG. 2, provides a measurable reduction in noise and thus provides a more efficient method of metal artifact reduction.

Figure 7D:
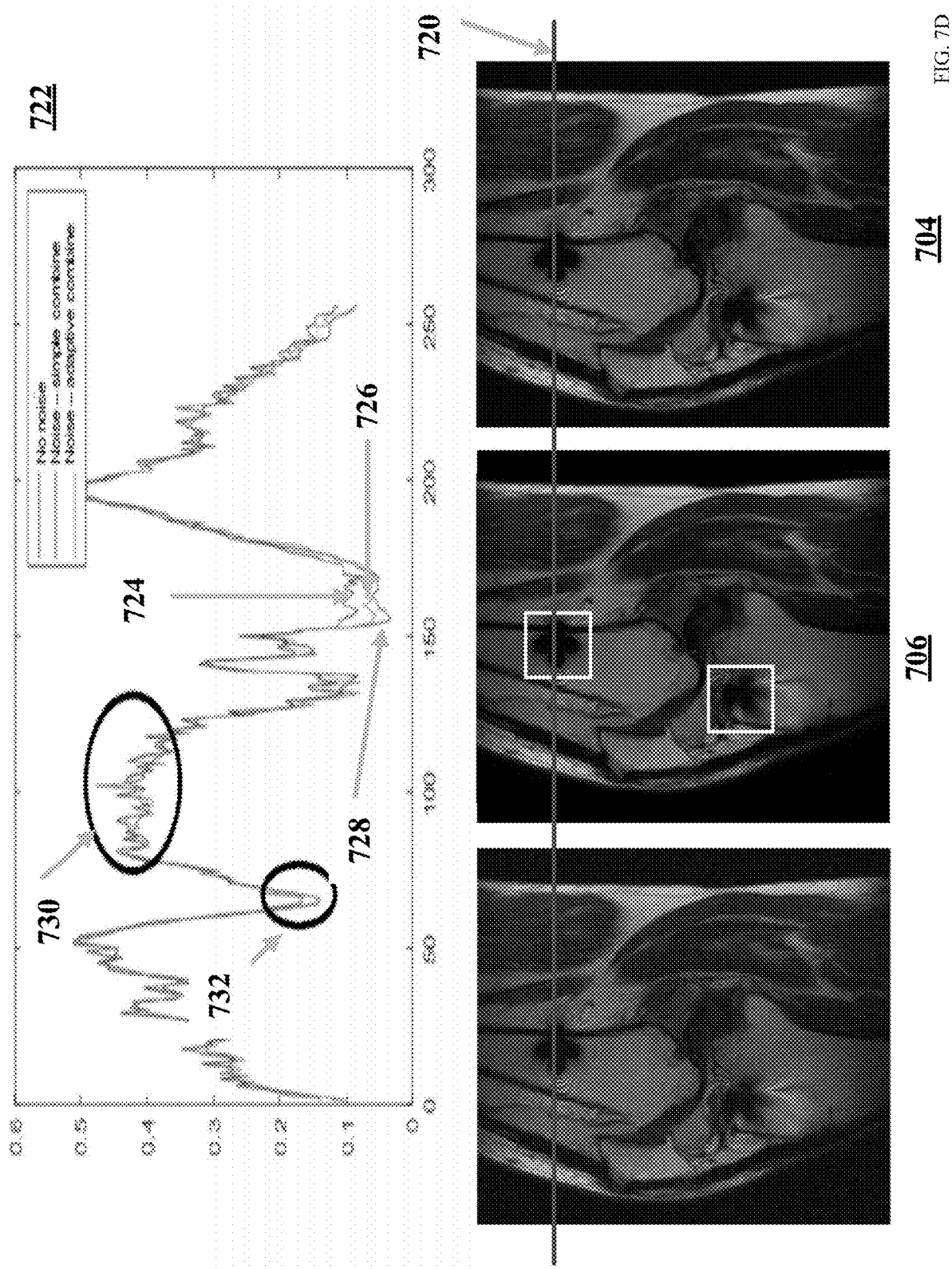
FIG. 7D illustrates a set of comparative signals corresponding to the upper highlighted areas on the images of FIG. 7A.

FIG. 7D illustrates signal generated at a position on the images 702, 704, and 706 of FIG. 7A. FIG. 7D illustrates a line 720 passing through the images 702, 704, and 706. Further, a graphical illustration 722 indicates signals generated corresponding to a location of the line 720 on the images 702, 704, and 706. By way of example, a signal 724 is generated corresponding to the location of the line 720 on the image 702, a signal 726 is generated corresponding to the location of the line 720 on the image 704, and the signal 728 is generated corresponding to the location of the line 720 on the image 706. The bubbles 730 and 732 highlight locations where the noise reduction methods yield very different results with the method of FIG. 2 wielding results closer to the target no noise signal. The 730 bubble demonstrates that the method of FIG. 2 preserves the high signal as well as the known method of FIG. 1. The 732 bubble shows that in a region with low signal (i.e., a region of noise), the method of FIG. 2 provides a result closer to the target no noise signal.

Figure 8:
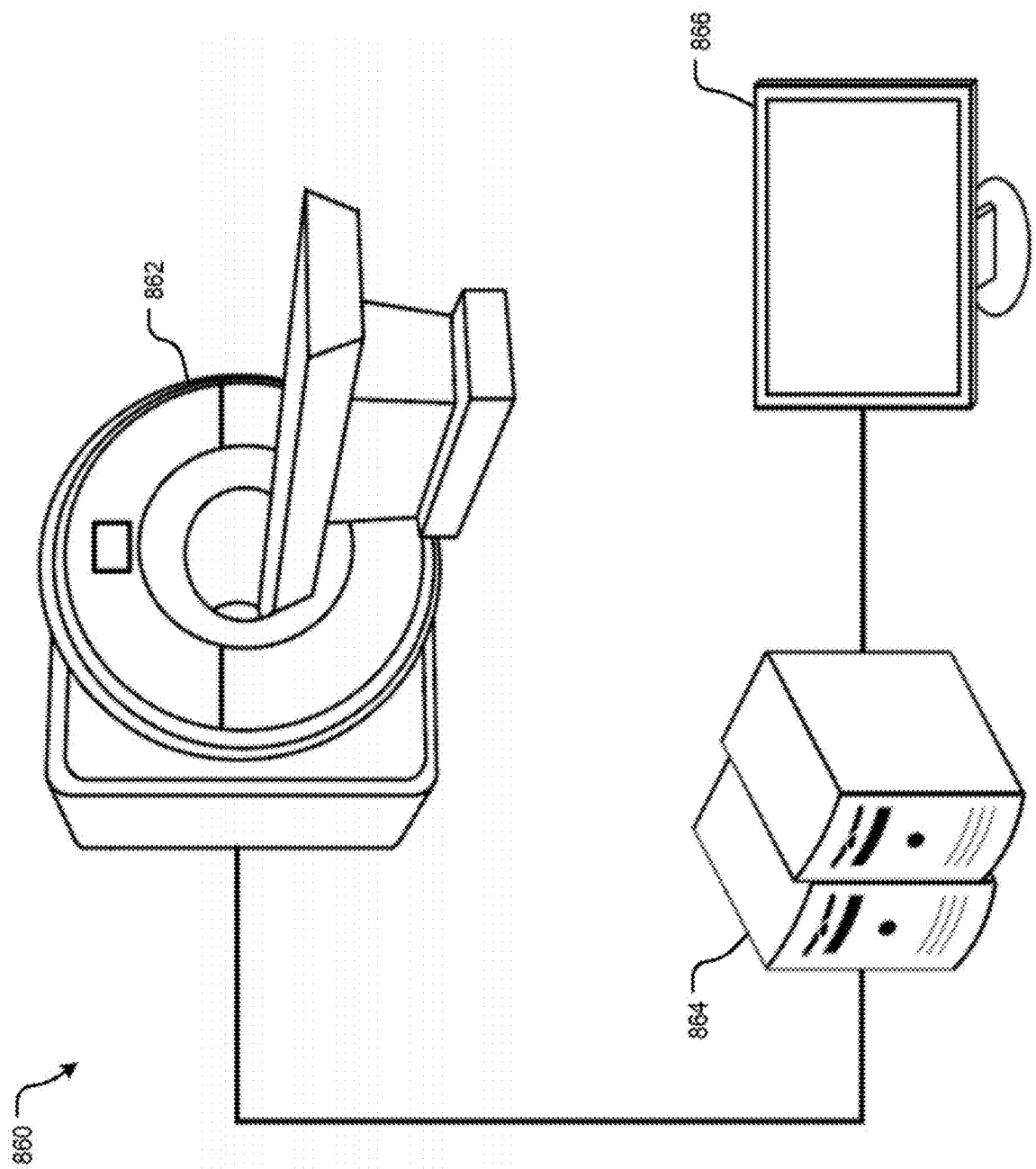
FIG. 8 is an illustration of a medical imaging system configured to acquire medical image data to be processed according to the teaching of the present disclosure.

FIG. 8 illustrates an example embodiment of a medical-imaging system 860 within which method 500 of the present disclosure can be implemented. The medical-imaging system 860 includes at least one scanning device 862, one or more image-generation devices 864, each of which is a specially-configured computing device (e.g., a specially-configured desktop computer, a specially-configured laptop computer, a specially-configured server), and a display device 866.

The scanning device 862 is configured to acquire scan data by scanning a region (e.g., area, volume, slice) of an object (e.g., a patient). The scanning modality may be, for example, magnetic resonance imaging (MRI), computed tomography (CT), positron emission tomography (PET), X-ray radiography, and ultrasonography.

The one or more image-generation devices 864 obtain scan data from the scanning device 862 and generate an image of the region of the object based on the scan data. To generate the image, for example during intermediate image generation or during final image reconstruction, the one or more image-generation devices 864 may perform a reconstruction process on the scan data. Examples of reconstruction processes include Compressed Sensing (CS), GRAPPA, CG-SENSE, SENSE, ARC, SPIRIT, and LORAKS.

In an embodiment, after the one or more image-generation devices 864 generate the image, the one or more image-generation devices 864 send the image to the display device 866, which displays the image.

In another embodiment, and further to the above, the one or more image-generation devices 864 may generate plural images from the same scan data. The one or more image-generation devices 864 may use different reconstruction processes to generate the two images from the same scan data, and one image may have a lower resolution than the other image. Additionally, the one or more image-generation devices 864 may generate an image.

Figure 9:
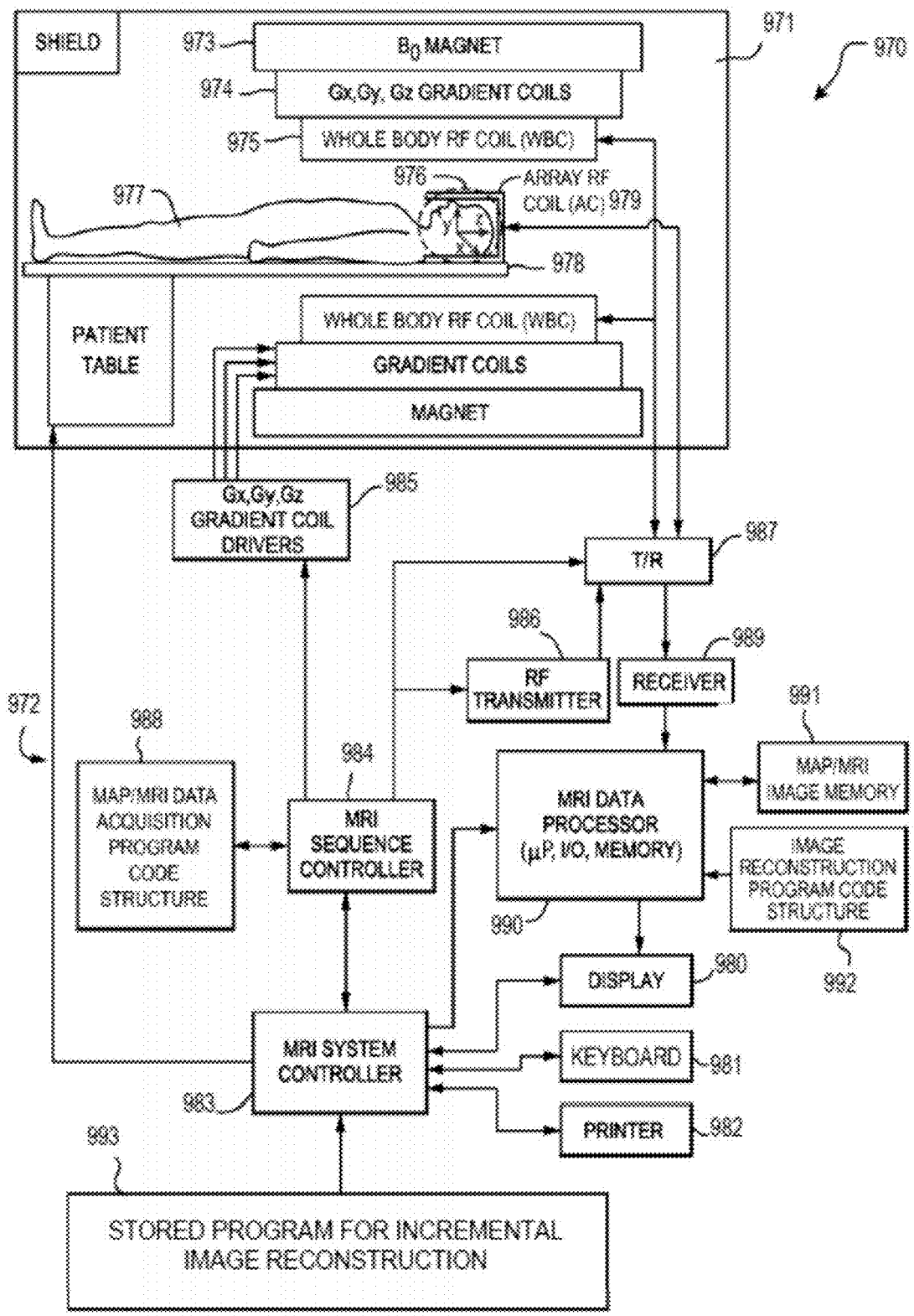
FIG. 9 is a schematic block diagram of various components of the medical imaging system of FIG. 8.

Referring now to FIG. 9, a non-limiting example of a magnetic resonance imaging (MRI) system 970 is shown. The MRI system 970 depicted in FIG. 9 includes a gantry 971 (shown in a schematic cross-section) and various related system components 972 interfaced therewith. At least the gantry 971 is typically located in a shielded room. The MRI system geometry depicted in FIG. 9 includes a substantially coaxial cylindrical arrangement of the static field $B_0$ magnet 973, a Gx, Gy, and Gz gradient coil set 974, and a large whole-body RF coil (WBC) assembly 975. Along a horizontal axis of this cylindrical array of elements is an imaging volume 976 shown as substantially encompassing the head of a patient 977 supported by a patient table 978.

One or more smaller array RF coils 979 can be more closely coupled to the patient's head (referred to herein, for example, as "scanned object" or "object") in imaging volume 976. As those skilled in the art will appreciate, compared to the WBC (whole-body coil), relatively small coils and/or arrays, such as surface coils or the like, are often customized for particular body parts (e.g., arms, shoulders, elbows, wrists, knees, legs, chest, spine, etc.). Such smaller RF coils are referred to herein as array coils (AC) or phased-array coils (PAC). These can include at least one coil configured to transmit RF signals into the imaging volume, and a plurality of receiver coils configured to receive RF signals from an object, such as the patient's head, in the imaging volume 976.

The MRI system 970 includes a MRI system controller 983 that has input/output ports connected to a display 980, a keyboard 981, and a printer 982. As will be appreciated, the display 980 can be of the touch-screen variety so that it provides control inputs as well. A mouse or other I/O device(s) can also be provided.

The MRI system controller 983 interfaces with a MRI sequence controller 984, which, in turn, controls the Gx, Gy, and Gz gradient coil drivers 985, as well as the RF transmitter 986, and the transmit/receive switch 987 (if the same RF coil is used for both transmission and reception). The MRI sequence controller 984 includes suitable program code structure 988 for implementing MRI imaging (also known as nuclear magnetic resonance, or NMR, imaging) techniques including parallel imaging. MRI sequence controller 984 can be configured for MR imaging with or without parallel imaging. Moreover, the MRI sequence controller 984 can facilitate one or more preparation scan (pre-scan) sequences, and a scan sequence to obtain a main scan magnetic resonance (MR) image (referred to as a diagnostic image). MR data from pre-scans can be used, for example, to determine sensitivity maps for RF coils 975 and/or 979 (sometimes referred to as coil sensitivity maps or spatial sensitivity maps), and to determine unfolding maps for parallel imaging.

The MRI system components 972 include an RF receiver 989 providing input to data processor 990 so as to create processed image data, which is sent to display 980. The MRI data processor 990 is also configured to access previously generated MR data, images, and/or maps, such as, for example, coil sensitivity maps, parallel image unfolding maps, distortion maps and/or system configuration parameters 991, and MRI image reconstruction program code structures 992 and 993.

In one embodiment, the MRI data processor 990 includes processing circuitry. The processing circuitry can include devices such as an application-specific integrated circuit (ASIC), configurable logic devices (e.g., simple programmable logic devices (SPLDs), complex programmable logic devices (CPLDs), and field programmable gate arrays (FPGAs), and other circuit components that are arranged to perform the functions recited in the present disclosure.

The processor 990 executes one or more sequences of one or more instructions, such as method 500 described herein, contained in the program code structures 992 and 993. Alternatively, the instructions can be read from another computer-readable medium, such as a hard disk or a removable media drive. One or more processors in a multi-processing arrangement can also be employed to execute the sequences of instructions contained in the program code structures 992 and 993. In alternative embodiments, hard-wired circuitry can be used in place of or in combination with software instructions. Thus, the disclosed embodiments are not limited to any specific combination of hardware circuitry and software.

Additionally, the term "computer-readable medium" as used herein refers to any non-transitory medium that participates in providing instructions to the processor 990 for execution. A computer readable medium can take many forms, including, but not limited to, non-volatile media or volatile media. Non-volatile media includes, for example, optical, magnetic disks, and magneto-optical disks, or a removable media drive. Volatile media includes dynamic memory.

Also illustrated in FIG. 9, and as referenced above, is a generalized depiction of an MRI system program storage (memory) 993, where stored program code structures are stored in non-transitory computer-readable storage media accessible to the various data processing components of the MRI system 970. As those in the art will appreciate, the program store 993 can be segmented and directly connected, at least in part, to different ones of the system 972 processing computers having most immediate need for such stored program code structures in their normal operation (i.e., rather than being commonly stored and connected directly to the MRI system controller 983).

Additionally, the MRI system 970 as depicted in FIG. 9 can be utilized to practice exemplary embodiments described herein below. The system components can be divided into different logical collections of "boxes" and typically comprise numerous digital signal processors (DSP), microprocessors and special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Furthermore, not only does the physical state of the processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of an image reconstruction process and/or sometimes an image reconstruction map (e.g., coil sensitivity map, unfolding map, ghosting map, a distortion map etc.) generation process, an array of computer-readable accessible data value storage sites in physical storage media will be transformed from some prior state (e.g., all uniform "zero" values or all "one" values) to a new state wherein the physical states at the physical sites of such an array vary between minimum and maximum values to represent real world physical events and conditions (e.g., the internal physical structures of a patient over an imaging volume space). As those skilled in the art will appreciate, such arrays of stored data values represent and also constitute a physical structure, as does a particular structure of computer control program codes that, when sequentially loaded into instruction registers and executed by one or more CPUs of the MRI system 970, causes a particular sequence of operational states to occur and be transitioned through within the MRI system 970.

Obviously, numerous modifications and variations are possible in light of the above teachings. It is therefore to be understood that within the scope of the appended claims, the invention may be practiced otherwise than as specifically described herein.

Embodiments of the present disclosure may also be as set forth in the following parentheticals.

(1) A method for correcting an artifact in magnetic resonance imaging (MRI) data, the method comprising acquiring plural slices along a slice direction of a scanned region associated with a body part, estimating a spatial extent of a signal dispersion of the acquired plural slices along the slice direction, and combining the signal of the acquired plural slices along the slice direction based on the estimated spatial extent of the signal dispersion to generate a reconstructed image of the scanned region.

(2) The method according to (1), further including, but not limited to, encoding each of the acquired plural slices spatially from a two-dimensional slice to a three-dimensional (3D) spatial volume slice to generate a series of 3D spatial volume slices.

(3) The method according to either one of (1) and (2), wherein combining the signal of the acquired plural slices includes, but is not limited to, combining the signal of the acquired plural slices by using at least one of a sum-of-squares calculation and a complex-valued sum.

(4) The method according to any one of (1) to (3), wherein estimating the spatial extent of the signal dispersion of the acquired plural slices along the slice direction includes, but is not limited to estimating the spatial extent of the signal dispersion of the acquired plural slices along the slice direction using a 3D spatial dipole response function.

(5) The method according to any one of (1) to (4), further including, but not limited to: identifying, from the acquired plural slices along the slice direction, a slice with a highest pixel intensity; and identifying at least one neighboring slice neighboring the slice with the highest pixel intensity based on a 3D spatial dipole response function, wherein combining the signal of the acquired plural slices along the slice direction based on the estimated spatial extent of the signal dispersion comprises combining (a) the signal of the slice with the highest pixel intensity and (b) the signal of the at least one neighboring slice.

(6) The method according to (5), wherein identifying the at least one neighboring slice neighboring the slice with the highest pixel intensity includes, but is not limited to, at least one neighboring slice neighboring the slice with the highest pixel intensity based on a 3D spatial dipole response function.

In addition, the present invention also includes the method of any of (1)-(6), wherein the artifact is a metal artifact.

(7) An apparatus for correcting an artifact in magnetic resonance imaging (MRI) data, the apparatus including, but not limited to: processing circuitry configured to: acquire plural slices along a slice direction of a scanned region associated with a body part; estimate a spatial extent of a signal dispersion of the acquired plural slices along the slice direction; and combine the signal of the acquired plural slices along the slice direction based on the estimated spatial extent of the signal dispersion to generate a reconstructed image of the scanned region.

(8) The apparatus according to (7), wherein the processing circuitry further includes, but is not limited to: processing circuitry configured to encode each of the acquired plural slices spatially from a two-dimensional slice to a three-dimensional (3D) spatial volume slice to generate a series of 3D spatial volume slices.

(9) The apparatus according to either one of (7) and (8), wherein the processing circuitry configured to combine the signal of the acquired plural slices includes, but is not limited to: processing circuitry configured to combine the signal of the acquired plural slices by using at least one of a sum-of-squares calculation and a complex-valued sum.

(10) The apparatus according to any one of (7) to (9), wherein the processing circuitry configured to estimate the spatial extent of the signal dispersion of the acquired plural slices along the slice direction includes, but is not limited to processing circuitry configured to estimate the spatial extent of the signal dispersion of the acquired plural slices along the slice direction using a 3D spatial dipole response function.

(11) The apparatus according to any one of (7) to (10), further including, but not limited to: processing circuitry configured to identify, from the acquired plural slices along the slice direction, a slice with a highest pixel intensity; and processing circuitry configured to identify at least one neighboring slice neighboring the slice with the highest pixel intensity based on a 3D spatial dipole response function, wherein the processing circuitry configured to combine the signal of the acquired plural slices along the slice direction based on the estimated spatial extent of the signal dispersion comprises the processing circuitry configured to combine (a) the signal of the slice with the highest pixel intensity and (b) the signal of the at least one neighboring slice.

(12) The apparatus according to (11), wherein the processing circuitry configured to identify the at least one neighboring slice neighboring the slice with the highest pixel intensity comprises processing circuitry configured to identify at least one neighboring slice neighboring the slice with the highest pixel intensity based on a 3D spatial dipole response function.

In addition, the present invention also includes the apparatus of any of (7)-(12), wherein the artifact is a metal artifact.

(13) A non-transitory computer-readable storage medium storing computer-readable instructions that, when executed by a computer, cause the computer to perform a method for correcting an artifact in magnetic resonance imaging (MRI) data, the method including, but not limited to any one of (1)-(6).

In addition, the present invention also includes the non-transitory computer-readable storage medium of any of (13), wherein the artifact is a metal artifact.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for correcting an artifact in magnetic resonance imaging (MRI) data, the method comprising:
    acquiring plural slices along a slice direction of a scanned region associated with a body part;
    identifying a first slice from the acquired plural slices along the slice direction, based on signal intensities of the acquired plural slices, the first slice indicating a location of a metal implant in the body part;
    identifying at least one second slice neighboring the first slice; and
    combining a signal of the first slice and a signal of the at least one second slice to generate a reconstructed image of the scanned region, wherein at least one slice other than the first slice and the at least one second slice in the acquired plural slices is not used for generating the reconstructed image while the first slice and the at least one second slice are used for generating the reconstructed image.

2. The method according to claim 1, further comprising:
    encoding each of the acquired plural slices spatially from a two-dimensional slice to a three-dimensional (3D) spatial volume slice to generate a series of 3D spatial volume slices.

3. The method according to claim 1, wherein combining the signal of the first slice and the signal of the at least one second slice comprises combining the signal of the first slice and the signal of the at least one second slice by using at least one of a sum-of-squares calculation and a complex-valued sum.

4. The method according to claim 1, wherein identifying the at least one second slice neighboring the first slice comprises identifying the at least one second slice neighboring the first slice using a 3D spatial dipole response function.

5. The method according to claim 1, wherein
    identifying the first slice comprises identifying, from the acquired plural slices along the slice direction, a slice with a highest pixel intensity as the first slice,
    identifying the at least one second slice comprises identifying at least one neighboring slice neighboring the slice with the highest pixel intensity as the at least one second slice, and
    combining the signal of the first slice and the signal of the at least one second slice comprises combining (a) the signal of the slice with the highest pixel intensity and (b) the signal of the at least one neighboring slice.

6. The method according to claim 5, wherein identifying the at least one neighboring slice neighboring the slice with the highest pixel intensity as the at least one second slice comprises identifying at least one neighboring slice neighboring the slice with the highest pixel intensity as the at least one second slice based on a 3D spatial dipole response function.

7. An apparatus for correcting an artifact in magnetic resonance imaging (MRI) data, the apparatus comprising:
processing circuitry configured to:
acquire plural slices along a slice direction of a scanned region associated with a body part;
identify a first slice from the acquired plural slices along the slice direction, based on signal intensities of the acquired plural slices, the first slice indicating a location of a metal implant in the body part;
identify at least one second slice neighboring the first slice; and
combine a signal of the first slice and a signal of the at least one second slice to generate a reconstructed image of the scanned region, wherein at least one slice other than the first slice and the at least one second slice in the acquired plural slices is not used for generating the reconstructed image while the first slice and the at least one second slice are used for generating the reconstructed image.

8. The apparatus according to claim 7, wherein the processing circuitry is configured to encode each of the acquired plural slices spatially from a two-dimensional slice to a three-dimensional (3D) spatial volume slice to generate a series of 3D spatial volume slices.

9. The apparatus according to claim 7, wherein the processing circuitry is configured to combine the signal of the first slice and the signal of the at least one second slice by using at least one of a sum-of-squares calculation and a complex-valued sum.

10. The apparatus according to claim 7, wherein the processing circuitry is configured to identify the at least one second slice neighboring the first slice using a 3D spatial dipole response function.

11. The apparatus according to claim 7, wherein
the processing circuitry is configured to identify the first slice by identifying, from the acquired plural slices along the slice direction, a slice with a highest pixel intensity as the first slice,
the processing circuitry is configured to identify the at least one second slice by identifying at least one neighboring slice neighboring the slice with the highest pixel intensity as the at least one second slice, and
the processing circuitry is configured to combine the signal of the first slice and the signal of the at least one second slice by combining (a) the signal of the slice with the highest pixel intensity and (b) the signal of the at least one neighboring slice.

12. The apparatus according to claim 11, wherein the processing circuitry is configured to identify the at least one neighboring slice neighboring the slice with the highest pixel intensity as the at least one second slice based on a 3D spatial dipole response function.

13. A non-transitory computer-readable storage medium storing computer-readable instructions that, when executed by a computer, cause the computer to perform a method for correcting an artifact in magnetic resonance imaging (MRI) data, the method comprising:
acquiring plural slices along a slice direction of a scanned region associated with a body part;
identifying a first slice from the acquired plural slices along the slice direction, based on signal intensities of the acquired plural slices, the first slice indicating a location of a metal implant in the body part;
identifying at least one second slice neighboring the first slice; and
combining a signal of the first slice and a signal of the at least one second slice to generate a reconstructed image of the scanned region, wherein at least one slice other than the first slice and the at least one second slice in the acquired plural slices is not used for generating the reconstructed image while the first slice and the at least one second slice are used for generating the reconstructed image.

* * * * *